US00PP19422P2

(12) United States Plant Patent
Chang

(10) Patent No.: US PP19,422 P2
(45) Date of Patent: Nov. 4, 2008

(54) STRAWBERRY PLANT CALLED 'TREASURE HARVEST'

(50) Latin Name: *Fragaria×ananassa Duchsne*
Varietal Denomination: Treasure Harvest

(76) Inventor: Peggy Pai-Chi Chang, 5983 Green Blvd., Naples, FL (US) 34116

( * ) Notice: Subject to any disclaimer, the term of this patent is extended or adjusted under 35 U.S.C. 154(b) by 0 days.

(21) Appl. No.: 11/801,180

(22) Filed: May 9, 2007

(51) Int. Cl.
*A01H 5/00* (2006.01)

(52) U.S. Cl. ..... Plt./208

(58) Field of Classification Search ..... Plt./208
See application file for complete search history.

*Primary Examiner*—Annette H Para
*Assistant Examiner*—S. B. McCormick-Ewoldt

(57) ABSTRACT

This invention is a new and distinct variety of strawberry plant named 'Treasure Harvest'. The fruit of 'Treasure Harvest' is very large, very firm, flavorful, glossy dark red on the outside, and moderately resistant to Anthracnose fruit rot diseases. The yield is high and tolerant to the heat when grown in west central and west southern Florida. Because of its high yield, firmness, long shell life and excellent fruit quality, 'Treasure Harvest' is recommended for fresh market. Due to its dark red color and firm fruit, 'Treasure Harvest' is also suitable for processing.

2 Drawing Sheets

Botanical classification: *Fragaria×ananassa Duchesne.*
Variety designation: 'Treasure Harvest'.

SUMMARY OF THE INVENTION

The new and distinct short day strawberry cultivar of the present invention was a part of an ongoing breeding program carried out at Naples, Fla. which has a subtropical climate. The seed resulted from the controlled cross between the strawberry plants 'Treasure' (U.S. Plant Pat. No. 12,414) and 'A4' (not patented).

The seeds resulting from this cross were germinated in a green house, and seedlings were transplanting to raised beds where they fruited during the season 2001–2002. 'Treasure Harvest' was selected for its high yield and superior fruit quality.

For the purpose of further evaluation, 'Treasure Harvest' has been asexually propagated by runners at Naples, Fla.; Kentville, Nova Scotia, Canada; and Laurel Springs, N.C.

During seasons 2005–06 & 2006–07 the new cultivar had been put in growers trialed in Plant City, Fla. During the trials this cultivar has shown its characteristics of high yield, large fruit size, good flavor, firm fruit, distinguishable glossy dark red fruit color, and moderate resistance to strawberry Anthracnose fruit rot disease.

The new cultivar of present invention can be distinguished from 'Treasure' and other commercial cultivars.

COMPARISON TO CLOSEST CULTIVARS

The commercial cultivar that we believe to be the closest comparison to 'Treasure Harvest' in appearance from those known to us is 'Treasure' (U.S. Plant Pat. No. 12,414). However, there are several characteristics of 'Treasure Harvest' that are different from or not possessed by 'Treasure'. Those are:

Size: The fruit size of 'Treasure Harvest' is distinguishable larger when compared with 'Treasure'.

Firmness: The fruit of 'Treasure Harvest' is distinguishable firmer when compared with 'Treasure'.

Plant size: The plant size of 'Treasure Harvest' is distinguishable larger than that of 'Treasure'.

Anthracnose fruit rot resistance: The plant of 'Treasure Harvest' has been screened with three species of strawberry anthracnose fruit rot: *Colletotrichum acutatum, C. fragariae* and *C. gloeosporioides.* 'Treasure Harvest' was found to be moderately resistant to anthracnose fruit rot, which is one of the major diseases in strawberry growth in the southeastern United States. In comparison, 'Treasure' is moderately susceptible to anthracnose fruit rot disease.

Bracts: There are no bracts on 'Treasure Harvest', but the frequency of bracts on the petioles of 'Treasure' is 63.6%.

DESCRIPTION OF THE NEW CULTIVAR

Figure 1:
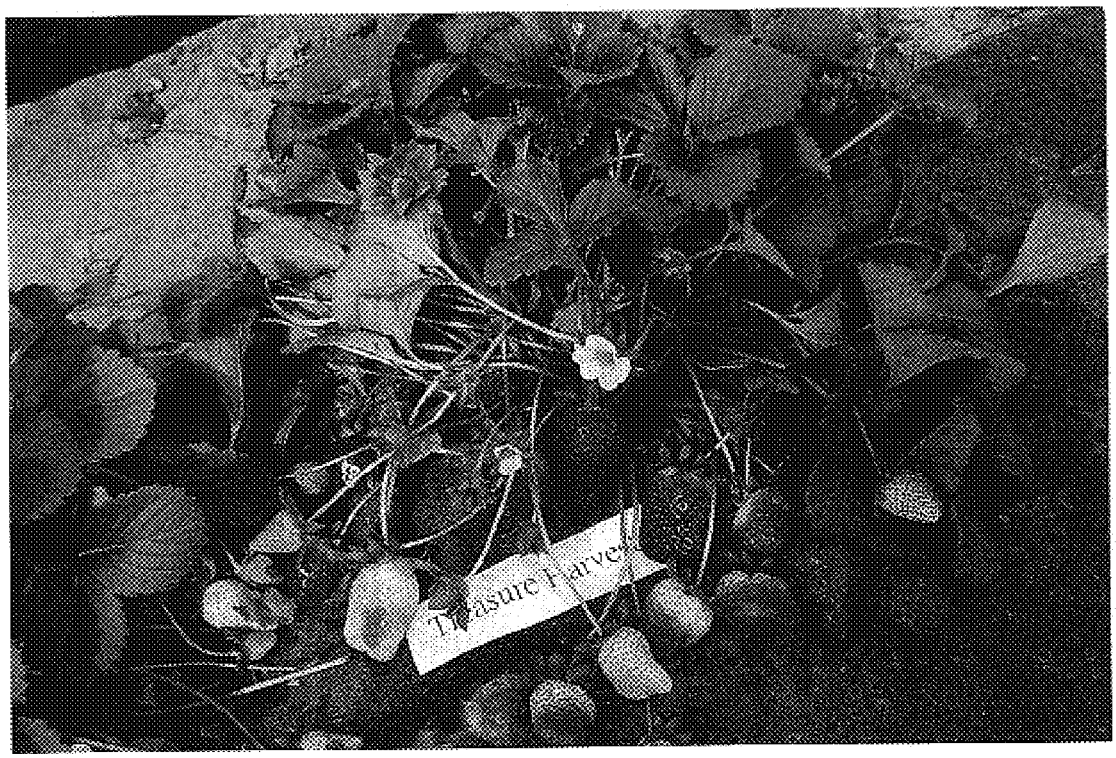
FIG. 1 shows the general flowering and fruiting characteristics of the plants during mid-season fruit production in Florida. Depicted are: a) a typical mature compound leaf, b) a representative complete flower during the mid-fruiting season, c) a partial fruiting truss including different stages of flowering and fruiting, and d) a typical mature fruit.
Figure 2:
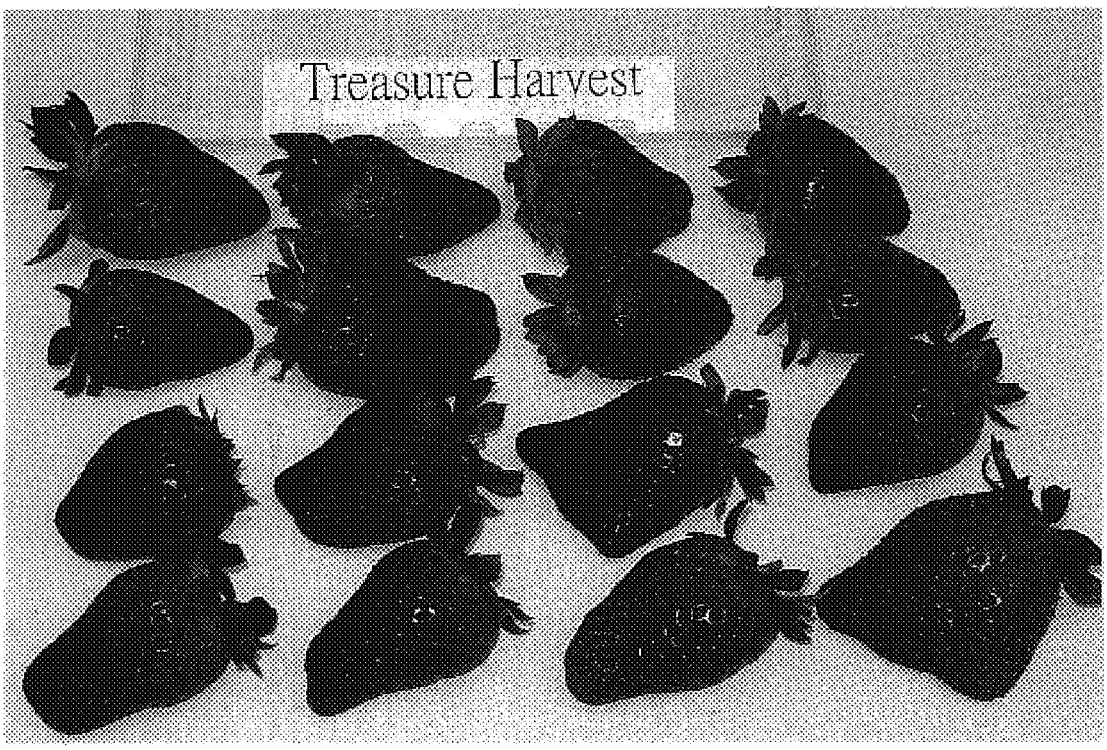
FIG. 2 shows plural fruit of the claimed plant reflecting the variation in fruit shape and size within market grade and shows seed and calyx placement relative to the fruit surface, as well as the attractive and uniform coloration of the ripe fruit at harvest stage.

'Treasure Harvest' is a new and distinctive short-day type strawberry cultivar which is the result of cross breeding between 'Treasure' (U.S. Plant Pat. No. 12,414) and 'A4' (not patented). The female parent 'Treasure' has the characteristics of large fruit size, high yield, early production, stable production, good fruit quality and good flavor. The male parent 'A4' has the characteristics of extra large fruit size, high yield, and vigorous plant. The novel cultivar 'Treasure Harvest' resembles the female parent in possessing high yield, stable production, good fruit quality, and good flavor and resembles the male parent in possessing extra large fruit and vigorous plant. 'Treasure Harvest' is superior to both parents in possessing firmer fruit, longer shelf life of fruit, and more resistance to Anthracnose fruit rot.

The distinctive characteristics of this new strawberry cultivar, described in detail below were observed upon its discovery and throughout the repeated test periods.

PLANTS AND FOLIAGE

The plants and foliage characteristics of 'Treasure Harvest', collected about 4 months after planting at Naples, Fla. Results are presented as below.

Plant & Foliage characteristics for 'Treasure Harvest'.

Plant:
- *Average size.*—Height (mm). — 198.; Diameter (mm). — 443.
- *Shape.*—Globose.
- *Vigor.*—Strong.
- *Root initiation.*—Good rooting, about 5 days to 1 week.

Foliage: Terminal leaflet:
- *Length* (*mm*).—70.
- *Width* (*mm*).—60.
- *Shape of terminal leaflet.*—Orbicular-ovate with serrulate margin.
- *Apex shape of leaflet.*—Rounded.
- *Base shape of leaflet.*—Rounded.
- *Venation pattern.*—Pinnate.
- *Vein color.*—2.5GY 7/8.
- *Color* (*Munsell color charts*).—Abaxial. — 5GY 3/4.; Adaxial. — 5GY 5/4.
- *Leaf pubescence.*—Moderate and direction is acropetal.
- *Serrations number of terminal leaflets* (*mean*).—19.

Petiole:
- *Length* (*mm*).—136.
- *Diameter* (*mm*).—3.
- *Color* (*Munsell color charts*).—5GY 7/6.
- *Pubescence.*—Heavy and direction is acropetal.

Petiolule:
- *Length* (*mm*).—8.
- *Diameter* (*mm*).—1.4.
- *Color* (*Munsell color charts*).—5GY 6/6.
- *Base angles of terminal leaflets* (*half blade*) (*degree*).—55.

Stolons:
- *Length* (*mm*).—250.
- *Number.*—Produced about 25 per plant.
- *Thickness* (*diameter, mm*).—2.
- *Pubescence.*—Moderate and direction is acropetal.

RESISTANCE TO DISEASE AND STRESS

The plant of 'Treasure Harvest' has been screened with three species of strawberry anthracnose fruit rot: *Colletotrichum acutatum, C. fragariae* and *C. gloeosporioides.* 'Treasure Harvest' was found to be moderately resistant to anthracnose fruit rot, which is one of the major diseases in strawberry growth in the southeastern United States. 'Treasure Harvest' is moderately tolerant to rain cracking and high and low temperatures.

FLOWERING AND FRUITING CHARACTERISTICS

The distinguishing flowering and fruiting characteristics of 'Treasure Harvest' plants were collected about 4–5 months after planting at Naples, Fla. Results are presented as below. The flowers are self-fertile and pollination is good when environmental condition is good. The center of the fruit is solid with little to no hollowing. The Canadian produced 'Treasure Harvest' plants typically begin to harvest about seven and half weeks after planting in Florida commercial production area.

Bud: At the stage of largest size, 1 day before flower opens.
- *Diameter* (*mm*).—36.
- *Length* (*mm*).—19.
- *Base shape of flower bud.*—Rounded.
- *Color* (*Munsell color charts*).—Upper: 5GY 4/6. Base: 5GY 6/4.

Flower: At fully open stage, 1 day after starting to open.
- *Diameter* (*mm*).—40.
- *Number of flower/cluster.*—3–5.
- *Fragrance.*—None.
- *Bloom time and period in specific location.*—The earliest buds open about 4 weeks after planting, for plants planted in mid-October. Plants bloom from November until May when observed at the breeding field in Naples, Fla.

Petals:
- *Length* (*mm*).—13.
- *Width* (*mm*).—13.
- *Shape.*—Obtuse. Apex: Obtuse. Base: Obtuse.
- *Color* (*no color chart given*).—White.
- *Texture.*—Smooth.
- *Margin.*—Entire.
- *Number.*—Mean: About 7. Range: 6–7.

Sepals:
- *Length* (*mm*).—15.
- *Width* (*mm*).—8.
- *Shape.*—Oblanceolate. Apex: Acute. Base: Cuneate.
- *Color* (*Munsell color charts*).—Abaxial: 5GY4/6. Adaxial: 5GY 6/4.
- *Number.*—Mean: 14. Range: 12–14.

Reproductive organs: Stamens:
- *Number.*—25.–38.
- *Length* (*mm*).—2–5.5.
- *Color* (*Munsell color charts*).—5Y 8/10.

Pistils:
- *Number & location.*—About 200–400 pistils attached on the surface of the receptacle.
- *Length* (*mm*).—1.8.
- *Color* (*Munsell color charts*).—2.5Y 8/12.

Fruit:
- *Shape.*—Long Conic and wedge.
- *Size & color.*—Green fruit: At maximum size about 1–2 days before starting to turn pink.
- *Size.*—Length (mm): 38. Diameter (mm): 31.
- *Color* (*Munsell color charts*).—Exterior: 2.5GY 8/6. Flesh: White (no color chart given).

Pink fruit: About 1–2 days before red.
- *Size.*—Length (mm): 44. Diameter (mm): 35.
- *Color* (*Munsell color charts*).—Exterior: 7.5R 5/14. Flesh: 7.5R 5/12.

Ripe fruit-red: About 1–2 days after pink.
- *Size.*—Length (mm): 45–55. Diameter (mm): 36–50. Weight (gram/fruit): Average: 28.4. Primary: 34.

*Color* (*Munsell color charts*).—Exterior: 6.25R 3/12. Flesh: 7.5R 4/12. Red color either from middle to both ends or from tip to shoulder.

*Firmness of fruit.*—The firmness of fruit, measured by Fruit Pressure Tester equipped with a 2.5 mm diameter plunger tip: Mean. — 476. Range. — 375–550.

*Sugar content of fruit.*—The sugar content or sweetness, measured as soluble solids: Mean. — 9.9. Range. — 9–11.4.

Pedicel:

*Of flowers.*—Flower at fully open stage.

*Length* (*mm*).—40–115.

*Diameter* (*mm*).—1.2.

*Color* (*Munsell color charts*).—5GY 7/6.

*Of fruits.*—Red ripe fruit stage.

*Length* (*mm*).—150–180.

*Diameter* (*mm*).—2.4.

*Color* (*Munsell color charts*).—5GY 6/8.

Seeds:

*Number* (*mean*)/*fruit.*—312.

*Shape.*—Oblong.

*Size.*—Length (mm): 1–1.5. Diameter (mm): 0.5–1.

*Color* (*Munsell color charts*).—2.5Y 8/8-5YR 6/10.

*Calyx position.*—Even/slight. Indent.

*Seed position.*—Even.

The yield of 'Treasure Harvest' is compared with that of 'Treasure' in Table 1.

TABLE 1

Data obtained from the 2005-06 fruiting season in Plant City, Florida

| | Yield (gram/plt) | |
|---|---|---|
| | Treasure Harvest' | Treasure' |
| December | 48.6 | 39.1 |
| January | 103.6 | 149.2 |
| February | 145.4 | 132.4 |
| March 1st-15th | 446.9 | 454.0 |
| Total | 744.5 | 774.7 |

We claim:

1. A new and distinct cultivar of strawberry plant named 'Treasure Harvest', as herein described and illustrated.

* * * * *